United States Patent [19]

Briet et al.

[11] 4,230,850

[45] Oct. 28, 1980

[54] 3-SUBSTITUTED-4-AMINOALKOXY-5,6-CONDENSED RING-2-PYRANONES

[75] Inventors: Philippe Briet; Jean-Jacques Berthelon; Jean-Claude Depin, all of Lyons, France

[73] Assignee: LIPHA, Lyonnaise Industrielle Pharmaceutique, Lyons, France

[21] Appl. No.: 18,875

[22] Filed: Mar. 9, 1979

Related U.S. Application Data

[63] Continuation of Ser. No. 768,745, Feb. 15, 1977, abandoned.

[30] Foreign Application Priority Data

Feb. 25, 1976 [FR] France .............................. 76 05234

[51] Int. Cl.³ .................. C07D 413/12; C07D 311/56

[52] U.S. Cl. ...................................... 544/151; 544/79; 544/375; 544/376; 546/196; 260/326.34; 260/326.5 CA; 260/326.5 D; 260/343.21; 260/343.45; 424/250; 424/248.55; 424/267; 424/274; 424/279

[58] Field of Search .................. 546/196; 544/79, 151, 544/375, 376; 260/326.34, 326.5 CA, 326.5 D, 343.21, 343.45

[56] References Cited

FOREIGN PATENT DOCUMENTS 2707746 9/1977 Fed. Rep. of Germany .

*Primary Examiner*—Henry R. Jiles
*Assistant Examiner*—R. W. Ramsuer
*Attorney, Agent, or Firm*—Browdy and Neimark

[57] ABSTRACT

Novel 3-substituted-4-aminoalkoxy-5,6-condensed ring-2-pyranones are disclosed as having utility as pharmacologically active compounds, in particular vasodilatory, hypotensive, anti-ischemic and anti-tussive activity. The compounds may be 3-phenyl-4-morpholinoalkoxy-coumarins. Administration may be by the oral or parenteral route. Intermediates useful in the production of these compounds are also disclosed.

6 Claims, No Drawings

3-SUBSTITUTED-4-AMINOALKOXY-5,6-CONDENSED RING-2-PYRANONES

This is a continuation of application Ser. No. 768,745 filed Feb. 15, 1977, abandoned.

This invention relates to substituted pyranones and is concerned with novel 3-substituted-4-aminoalkoxy-5,6-condensed ring-2-pyranones and processes for preparing them. It also relates to the use of these pyranones in the field of therapeutics.

The substituted pyranones of the invention are represented by the general formula:

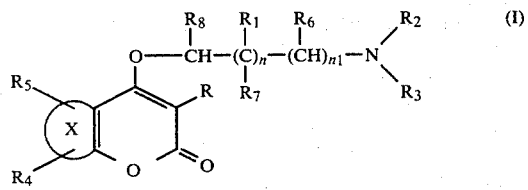

wherein:
n is 0 or 1;
$n_1$ is 0 or 1;
R is lower alkyl, phenyl, phenyl substituted by at least one halogen atom or lower alkoxy group, or benzyl;
$R_1$ is hydrogen, a hydroxy or lower alkyl group, or a 3,4,5-trialkoxybenzoyloxy radical;
$R_2$ is a straight-chain or branched lower alkyl group;
$R_3$ is hydrogen or lower alkyl; or
$R_1$ and $R_2$ are joined together to form with the adjacent nitrogen atom a saturated heterocyclic ring with n being 1 and $n_1$ being 0, or
$R_2$ and $R_3$ are joined together to form with the adjacent nitrogen atom a saturated heterocyclic ring optionally containing a further hetero atom;
X represents a benzene, cyclohexene, cycloheptene, cyclooctaene, cyclododecaene, naphthalene, dihydronaphthalene, 2-phenylidene or diphenyl ring;
$R_4$ is hydrogen or a substituent selected from halogen atoms and hydroxy, straight-chain or branched lower alkyl, lower alkoxy, morpholinoalkoxy and aryl groups;
$R_5$ is a substituent selected from hydrogen hydroxy, straight-chain or branched lower alkyl, lower alkoxy and morpholinoalkoxy groups;
$R_6$ is hydrogen or a lower alkyl group;
$R_7$ is hydrogen or a lower alkyl group; and
$R_8$ is hydrogen or a lower alkyl group.

The compounds of formula I have been found to possess pharmacological activity and in particular vasodilatory, hypotensive, anti-ischemic and anti-tussive properties.

Thus the pharmaceutically acceptable acid addition salts of the compounds of formula I, which may be formed with inorganic or organic acids, also form part of the present invention.

One group of compounds falling within the class defined by formula I is that represented by the general formula:

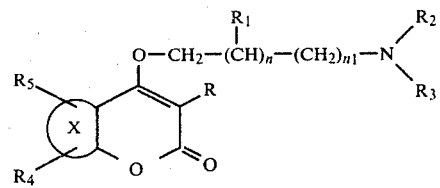

and the pharmaceutically acceptable acid addition salts thereof,
wherein:
n is 0 or 1;
$n_1$ is 0 or 1;
R is lower alkyl, phenyl, phenyl substituted by at least one halogen atom or lower alkoxy group, or benzyl;
$R_1$ is hydrogen, a hydroxy or lower alkyl group, or a 3,4,5-trialkoxybenzoyloxy radical;
$R_2$ is a straight-chain or branched lower alkyl group;
$R_3$ is hydrogen or lower alkyl; or
$R_1$ and $R_2$ are joined together to form with the adjacent nitrogen atom a saturated heterocyclic ring with n being 1 and $n_1$ being 0, or
$R_2$ and $R_3$ are joined together to form with the adjacent nitrogen atom a saturated heterocyclic ring optionally containing a further hetero atom;
X represents a benzene, cyclohexene, cycloheptene, cyclooctaene, cyclododecaene, naphthalene, dihydronaphthalene, 2-phenylindene or diphenyl ring;
$R_4$ is hydrogen or a substituent selected from hydroxy, straight-chain or branched lower alkyl, lower alkoxy and morpholinoalkoxy groups; and
$R_5$ is a substituent selected from hydrogen, hydroxy, straight-chain or branched lower alkyl, lower alkoxy and morpholinoalkoxy groups.

A preferred group of compounds falling within the class defined by formula I is that in which R is phenyl and $R_2$ and $R_3$ are joined together to form with the adjacent nitrogen atom a morpholino ring.

The preparation of the compounds of formula I may be accomplished in accordance with the reaction sequence as set out below, in which R, $R_1$, $R_2$, $R_3$, $R_4$, $R_5$, $R_6$, $R_7$, $R_8$, X, n and $n_1$ have the same meanings as in formula I:

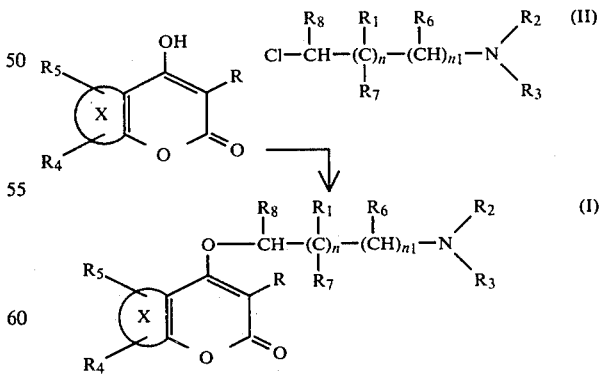

The reaction is carried out in an organic solvent and in the presence of a base, for example an alkali metal carbonate or bicarbonate. A ketone may be used as the organic solvent and the use of methyl isobutyl ketone has been found to be advantageous. The reaction is generally carried out at reflux temperature and the resulting product can be isolated by methods which are well known in the art. The product in free base form may be reacted in a known manner with an appropriate acid to form a desired pharmaceutically acceptable acid addition salt.

The compounds of formula I in which $R_1$ is OH, $R_6$, $R_7$ and $R_8$ are all hydrogen and n is 1 may be prepared via the epoxide (formula III) obtained by replacing the chlorinated amine in the preceding sequence by epichlorohydrin or epibromohydrin, as shown in the following reaction scheme:

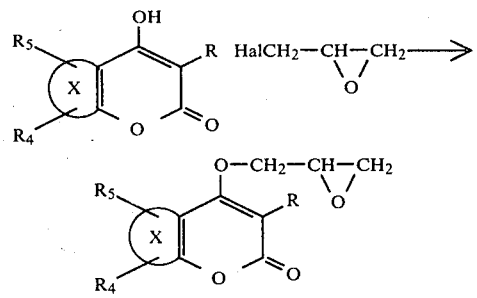

wherein Hal represents chlorine or bromine.

The reaction of the epoxide of formula III with an amine of the general formula:

in which $R_2$ and $R_3$ have the same meanings as in formula I, gives the required compounds.

For obtaining the compounds of formula I in which $R_1$ is OH, $R_6$, $R_7$ and $R_8$ are all hydrogen and n is 1, it is sometimes advantageous to alkylate the appropriate hydroxypyrone of formula II with an aminoepoxypropane (formula IV below) by heating in a suitable organic solvent, such as a ketone of high boiling point.

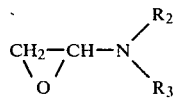

The epoxide represented by formula IV may be obtained by direct action of epichlorohydrin on the amine

in the presence of water.

The compounds of formula I in which $R_1$ is a 3,4,5-trialkoxybenzoyloxy radical may be obtained from the corresponding compounds of formula I in which $R_1$ is a hydroxy group by reaction in an organic solvent with 3,4,5-trialkoxybenzoyl chloride in the presence of a base.

Of the intermediate products represented by formula II above, those in which R is phenyl, 3,4-dichlorophenyl or 4-fluorophenyl; X is a benzene, chlorobenzene, cyclohexene, phenyl cyclohexane, 6-tert.butylcyclohexene, cycloheptene, cylooctaene, dihydronaphthalene or 2-phenylindene ring and $R_4$ and $R_5$ have the same meanings as in formula I, are believed to be novel compounds and as such form part of the invention. The 4-[2',3')-epoxy propoxy]-3-phenyl-coumarin is also a new intermediate product which is especially necessary in the preparation of 4-(3'-isopropylamino-2'-hydroxypropoxy)-3-phenyl coumarin.

The compounds of the invention have pronounced pharmacological activity, which makes them of potential use as vasodilators, hypotensive agents, anti-ischemic agents or anti-tussive agents. The pharmacological investigation of these compounds has been carried out in the following manner.

On the coronary level, the compounds of the invention have proved to be powerful dilators. The rate of flow of the intraventricular coronary artery was measured with an electromagnetic flow meter on the anaesthetised dog.

The different test compounds, administered intravenously, have caused considerable increases in the rate of flow, as reported in Table I below (the standard used for comparison being 2,6-di-[di-(2-hydroxyethyl)amino]-4,8-dipiperidinopyrimido-[5,4-d]-pyrimidine, which has the B.P.C. approved name of "Dipyridamole").

TABLE I

| Compounds | Coefficient related to Dipyridamol |
|---|---|
| Dipyridamol | 100 |
| Example 2 | 150 |

Example 23

TABLE I-continued

| Compounds | Coefficient related to Dipyridamol |
|---|---|
| 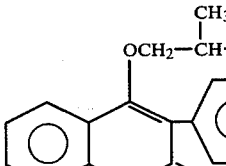 | 300 |
| | 150 |
| 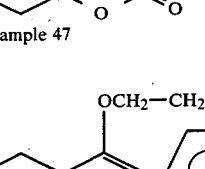 Example 16 | 100 |
| Example 12 | 250 |
| 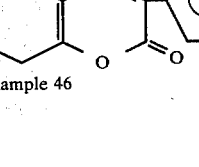 | 150 |

The compounds of the invention are capable of inhibiting the phosphodiesterase of cyclic AMP (adenosine monophosphate).

Table II gives the inhibition indices ($ID_{50}$), measured in vitro, for some of the compounds of the invention.

TABLE II

| Compounds | $ID_{50}$ |
|---|---|
| Papaverine | |
| Example 4 | 150 |
| Example 19 | |

TABLE II-continued

| Compounds | $ID_{50}$ |
|---|---|
| Example 47 | 600 |
| Example 46 | 200 |

TABLE II-continued

| Compounds | ID$_{50}$ |
|---|---|
| Example 3: structure with O—CH$_2$—CH(CH$_3$)—CH$_2$—N(morpholino), cyclohexene fused to chromone-like system | 600 |
| structure with O—CH$_2$—CH$_2$—N(piperidino), chromone-like with phenyl | 150 |

Anti-hypertensive (hypotensive) activity has been found with the compounds of the invention. With rats made hypertensive by the Goldblatt technique (M. GOLDBLATT, J. LUNCH, R. F. MANZAL and W. W. SUMMERVILLE, J. of Exper. Med. 1934, 59, 347–379), decreases in hypertension were recorded after oral administration of the test compound. By way of example, Table III gives the decreases obtained with some of the compounds.

TABLE III

| Compounds | Decrease in hypertension in mm.Hg., 3 to 5 hours after administration |
|---|---|
| Example 2: structure OCH$_2$—CH$_2$—N(morpholino), chromone with phenyl | −34 (HS) |
| Example 19 / Example 35: structure O—CH$_2$—CH(CH$_3$)—CH$_2$—N(morpholino) | −18(S) |
| Example 45: structure O—CH$_2$—CH$_2$—N(morpholino) | −44 (HS) |
| structure with phenyl-substituted indane fused system, O—CH$_2$—CH$_2$—N(morpholino) | −49 (HS) |

The compounds of the invention have been found to have marked vasodilatory activity, which is proved by measuring, with the aid of an electromagnetic flow meter, the rate of flow of a femoral artery in the dog anaesthetised with sodium ethyl methyl butyl barbiturate ("Pentobarbital").

The coefficients given in Table IV are expressed relatively to papaverine, which is given the coefficient 1, for the femoral dilation which it causes under similar conditions.

TABLE IV

| | Coefficient/Papaverine |
|---|---|
| Example 37 / Example 20: structure OCH$_2$—CH(OH)—CH$_2$—N(piperidino), chromone with phenyl | 12 |

TABLE IV-continued
| | Coefficient/Papaverine |
|---|---|
| 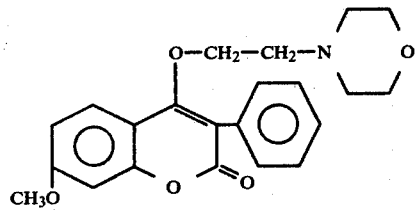
Example 21 | 12 |
| 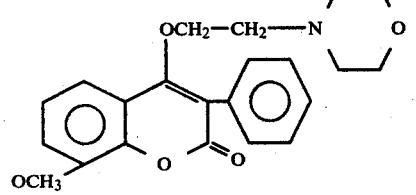
Example 35 | 13 |
| 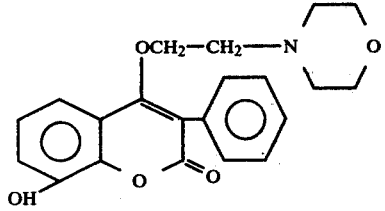
Example 45 | 8 |
| (implied) | 12 |
| 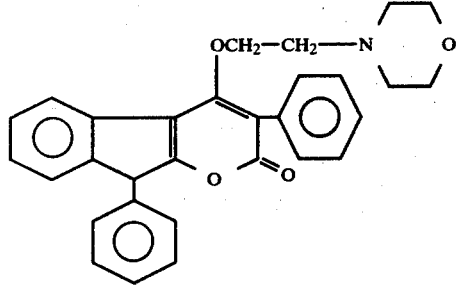
Example 23 | 60 |
| 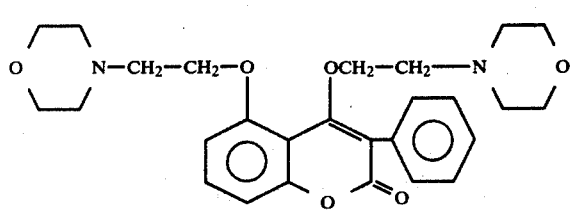
Example 4 | 6 |

TABLE IV-continued
| | Coefficient/Papaverine |
|---|---|
| 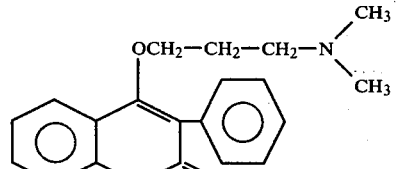 | 60 |
Likewise, the vasodilation produced by the compounds of the invention is measured by means of the vertebral rate of flow in the anaesthetised dog. Some results are set out in Table V by way of example.
TABLE V
| Compounds | Coefficient/Papaverine |
|---|---|
| Papaverine | 1 |
| Example 2 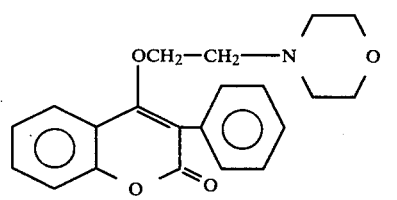 | 2 |
| Example 19 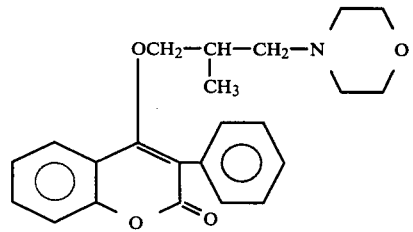 | 3 |
| Example 27 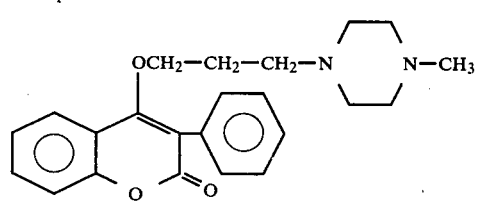 | 3 |
| Example 4 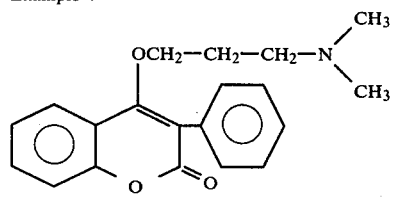 | 6 |
| Example 37 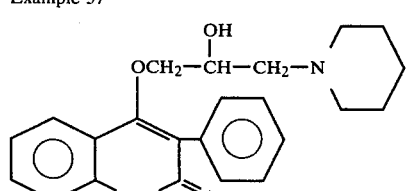 | 9 |
| Example 23 | |

TABLE V-continued

| Compounds | Coefficient/ Papaverine |
|---|---|
| Example 21 (structure: chromen-2-one with two OCH₂—CH₂—N-morpholino substituents and phenyl) | 4.5 |
| Example 35 (structure: chromen-2-one with OCH₂—CH₂—N-morpholino, OCH₃, phenyl) | 5 |
| (structure: chromen-2-one with OCH₂—CH₂—N-morpholino and OH, phenyl) | 10 |
| Example 5 (structure: hexahydro-chromen-2-one with OCH₂—CH₂—N-morpholino and phenyl) | 5.5 |
| (structure: chromen-2-one with three morpholino-ethoxy groups, CH₂—CH₂—CH₂—CH₃) | 2 |

As well as the vasodilatory activity, a strong protective action against the effects of anoxia has been found for the compounds of the invention. By way of example, Table VI indicates as a percentage the increase in the survival time caused by oral administration of certain compounds to mice placed in a confined atmosphere.

TABLE VI

| Compounds | Average % increase in survival time |
|---|---|
| Example 7 | |
| Example 19 (structure: chromen-2-one with OCH₂—CH₂—N-morpholino and 4-Br-phenyl) | +50 |

TABLE VI-continued

| Compounds | Average % increase in survival time |
|---|---|
| Example 2 (structure with OCH₂-CH(CH₃)-CH₂-N-morpholine) | +46 |
| Example 30 (structure with O-CH₂-CH₂-N-morpholine) | +41 |
| Example 14 (structure with OH and O-CH₂-CH₂-N-morpholine) | +65 |
| Example 9 (structure with O-CH₂-CH₂-N-morpholine) | +50 |
| Example 11 (structure with OCH₂-CH₂-N-morpholine and CH₃) | +30 |
| Example 46 (structure with OCH₂-CH₂-N-morpholine and F) | +45 |
| (structure with O-CH₂-CH(CH₃)-CH₂-N-morpholine) | +40 |

The compounds of the invention have been found to have marked anti-tussive properties, which are shown for example by the citric acid aerosol test on the guinea pig (CHARLIER, Arch. Int. Pharmacodynamie 134, 306–327, 1961).

The compounds of the invention were compared with codeine. Table VII gives by way of example results obtained with some compounds.

TABLE VII

| Compounds (administered in equitoxic dose per os) | % inhibition on average of number of coughs |
|---|---|
| Codeine | 55 |
| Example 30 | 85 |
| Example 19 (with Cl, Cl) | 47 |
| Example 51 | 64 |
| Example 19 | 60 |
| Example 44 | 52 |
| (final structure) | 48 |

The compounds of the invention will normally be employed for therapeutic purposes in the form of a pharmaceutical composition comprising as an essential active ingredient a compound of formula V, or a pharmaceutically acceptable acid addition salt thereof, in association with a pharmaceutical carrier or excipient therefor. The composition can advantageously be made up in the form of a dosage unit appropriate to the desired mode of administration. Thus for oral administration the dosage unit may be a pill, tablet or capsule, whilst for parenteral administration the dosage unit may be an injectable solution packaged in a container such as an ampoule. Pills may be gelatin-coated or coated with a cellulose derivative to make them gastro-resistant. The pharmaceutical composition may alternatively be in the form of, for example, an aqueous suspension, a syrup or an aerosol. The active ingredient may be present in the composition in an amount such that a daily dose of from 10 mg. to 1 g. of the active ingredient can be achieved by administration of one or more dosage units.

The compounds of the invention which possess an asymmetrical carbon atom in the aminoalkoxy side-chain, can be separated into optical isomers by processes known in the art, for example, fractional crystallisation of salts formed with optically active acids. It will be understood therefore that the present invention covers not only the optically inactive racemic mixtures of those compounds but also the individual optically active isomers where these exist.

The following non-limitative Examples illustrate the preparation of compounds in accordance with the invention.

EXAMPLE 1

4-(2'-Diethylaminoethoxy)-3-phenyl-coumarin 11.9 g. (0.05 mol) of 3-phenyl-4-hydroxy-coumarin, 8.3 g. (0.06 mol) of anhydrous potassium carbonate and 200 ml. of methyl isobutyl ketone are placed in a dry reactor. The mixture is brought while stirring for 1 hour to 70° C. 0.5 g. of potassium iodide is then added, followed by dropwise addition of a solution of 8.8 g. (0.065 mol) of 2-diethylamino-1-chlorethane in 20 ml. of methyl isobutyl ketone.

The mixture is then refluxed for 8 hours. The resulting insoluble mineral substance is filtered hot and the filtrate obtained is evaporated under vacuum. 16 g. of a yellow oil are obtained, which cannot be crystallised. Yield 84% (theoretical yield 19 g.).

Hydrochloride

The oil is solubilised in 200 ml. of isopropanol and the theoretical quantity of HCl gas is added at 0° C.

By addition of ether, a thick oil precipitates. It is stood for one night at −20° C. under ether, the precipitate obtained is isolated and recrystallised from acetone and then from isopropanol. M.P. 154° C.

EXAMPLE 2

4-(2'-Morpholinoethoxy)-3-phenyl-coumarin

By causing 100 g. (0.42 mol) of 3-phenyl-4-hydroxy-coumarin and 86.8 g. (0.55 mol) of 2-morpholino-1-chlorethane to react in the manner described in Example 1, 119 g. of a white solid are obtained. M.P. 97° C. (isopropanol), yield 80% (theoretical yield 147 g.).

Maleate

Prepared by treating the base in solution in acetone with the theoretical quantity of maleic acid. M.P. 162° (methanol).

EXAMPLE 3

4-(2'-Piperidinoethoxy)-3-phenyl-coumarin 10 g. (0.042 mol) of 3-phenyl-4-hydroxy-coumarin and 10.1 g. (0.55 mol) of 2-piperidino-1-chlorethane hydrochloride are caused to react in the manner described in Example 1. 10.8 g. of a yellow oil are obtained, which cannot be crystallised. Yield 73% (theoretical yield 14.7 g.).

Oxalate

This is obtained by treating the base in solution in acetone with the theoretical quantity of oxalic acid. M.P. 171° C. (methanol).

EXAMPLE 4

4-(3'-Dimethylaminopropoxy)-3-phenyl-coumarin

By treating 10 g. (0.042 mol) of 3-phenyl-4-hydroxy-coumarin with 87 g. (0.055 mol) of 3-dimethylamino-1-chloropropane hydrochloride as described in Example 1, there are obtained 8.1 g. of a yellow oil which cannot be crystallised. Yield 59% (theoretical yield 13.6 g.).

Oxalate

This is obtained in the manner described in Example 3. M.P. 191° C. (dimethylformamide-ethanol: 4/6).

EXAMPLE 5

3-Butyl-4,5,7-tri(2'-morpholinoethoxy)-coumarin 7.5 g. (0.03 mol) of 3-butyl-4,5,7-trihydroxy-coumarin are treated with 17.5 g. (0.117 mol) of 2-morpholino-1-chlorethane, as in Example 1. A beige-coloured solid is obtained. M.P. 131° C. (ethanol). Weight 7.7 g.; yield 45% (theoretical yield 17.7 g.).

Trioxalate

This is obtained as described in Example 3. M.P. 131° C. (methanol).

EXAMPLE 6

3-Phenyl-4-(2'-morpholinoethoxy)-benzo-(7,8)-coumarin 8.7 g. (0.03 mol) of 3-phenyl-4-hydroxy-benzo-(7,8)-coumarin are treated according to Example 1 with 5.83 g. (0.039 mol) of 2-morpholino-1-chlorethane. 10 g. of a beige-coloured solid are obtained. M.P. 140° C. (acetone). Yield 89.4% (theoretical yield 12.3 g.).

Hydrochloride

The base is solubilised in the theoretical quantity of aqueous HCl at boiling point, and the mixture obtained cooled to room temperature. The solid formed is then isolated. M.P. 190° C. (MeOH).

EXAMPLE 7

3-(4'-Bromophenyl)-4-(2''-morpholinoethoxy)-coumarin 5.2 g. (0.0164 mol) of 3-(4'-bromophenyl)-4-hydroxy-coumarin are treated in accordance with Example 1 with 3.2 g. (0.0214 mol) of 2-morpholino-1-chlorethane. After evaporation of the methyl isobutyl ketone, the resulting solid is taken up in 100 ml. of a 5% solution of sodium bicarbonate at boiling point. The solution is filtered and recrystallised. Weight 3.2 g.; yield 45% (theoretical yield 7.1 g.); M.P. 151° C.

Hydrochloride

The base is solubilised in chloroform. An alcoholic solution of HCl is added at 0° C. until the pH is 1. The solvents are evaporated under vacuum and recrystallisation takes place. M.P. 170°–180° C. (methanol).

EXAMPLE 8

4-(2'-Pyrrolidinoethoxy)-3-phenyl-coumarin

In accordance with Example 1, 10 g. (0.042 mol) of 3-phenyl-4-hydroxy-coumarin are caused to react with 9.3 g. (0.055 mol) of 2-pyrrolidino-1-chlorethane. After evaporation of the methyl isobutyl ketone, the pasty residue is taken up under heat in 150 ml. of a 5% solution of sodium bicarbonate, this being followed by cooling and extraction with chloroform. The substance obtained is dried over $Na_2SO_4$ and the chloroform is evaporated under vacuum. A brown oil is obtained. Weight 6.5 g.; yield 46% (theoretical yield 14.1 g.).

Maleate

This is obtained as described in Example 2. M.P. 125°–130° C. (methanol).

EXAMPLE 9

3-Methyl-4-(2'-morpholinoethoxy)-coumarin 8.8 g. (0.05 mol) of 3-methyl-4-hydroxy-coumarin are solubilised in 200 ml. of methyl isobutyl ketone at 80° C., and then, at this temperature, there are added 8.3 g. (0.06 mol) of anhydrous potassium carbonate and 0.5 g. of potassium iodide. The mixture is left for 1 hour at 80° C. while stirring. In 1 hour, there is added a solution of 9.8 g. (0.065 mol) of 2-morpholino-2-chlorethane in 50 ml. of methyl isobutyl ketone. The substance is then refluxed for 8 hours, filtered while hot and evaporated under vacuum. The oil which is obtained is taken up under heat in 200 ml. of a 5% solution of sodium bicarbonate, whereafter it is cooled, and extracted with 3×100 ml of ether. It is dried over $NaSO_4$ and then the ether is evaporated under vacuum. A brown oil is obtained which cannot be crystallised. Weight 10 g.; yield 67% (theoretical yield 14.9 g.).

Oxalate

This is obtained in the manner described in Example 3. M.P. 164°–167° C. (methanol).

EXAMPLE 10

3-(3',4'-Dichlorophenyl)-4-(2''-morpholinoethoxy)-coumarin

The preparation is carried out, using the following intermediates:

(a) 3-(3',4'-Dichlorophenyl)-4-hydroxy-coumarin 33.8 g. (0.21 mol) of 4-hydroxy-coumarin, 140 ml. of acetone, 40 g. of sodium acetate and 6.6 g. of cuprous chloride are placed in a one-liter reactor. The mixture is brought to a temperature lower than 5° C. There are then added dropwise a solution of the diazonium chloride of 3,4-dichloro-aniline, prepared from 32.4 g. (0.2 mol) of 3,4-dichloro-aniline, 80 ml. of concentrated hydrochloric acid, 120 ml. of water and 20 g. (0.33 mol) of sodium nitrite. A slight liberation of nitrogen is found. The substance is left for one hour between −8° C. and −5° C. and it is then brought for one hour to 50° C. The acetone is then evaporated under vacuum. A pH value of 1 is adjusted. The chestnut-coloured precipitate is taken up under heat in 2 liters of a 5% solution of sodium bicarbonate, followed by filtration and then the filtrate is acidified with HCl. The product obtained is recovered, washed with water, dried and recrystallised from a mixture of ethanol and water (70–30). A chestnut-coloured product is obtained. Weight 9.8 g.; yield 16% (theoretical yield 51.4 g.); M.P. 262° C.

(b) 3-(3',4'-Dichlorophenyl)-4-(2''-morpholinoethoxy)-coumarin

In accordance with Example 9, 9 g. (0.03 mol) of 3-(3',4'-dichlorophenyl)-4-hydroxy-coumarin and 6 g. (0.04 mol) of 2-morpholino-1-chlorethane are caused to react. 10 g. of a yellow oil are obtained, which cannot be crystallised. Yield +79% (theoretical yield 12.6 g.).

Maleate

Obtained as indicated in Example 2. M.P. 157°–159° C. (ethanol).

EXAMPLE 11

3-(4'-Fluorophenyl)-4-(2''-morpholinoethoxy)-coumarin 6 g. (0.023 mol) of 3-(4'-fluorophenyl)-4-hydroxy-coumarin are treated according to Example 8 with 4.55 g. (0.030 mol) of 2-morpholino-2-chlorethane. After evaporation of the chloroform, the residue is recrystallised from ethanol. Weight 4 g.; yield 47% (theoretical yield 8.5 g.). M.P. 108° C. (ethanol).

Maleate

Obtained as indicated in Example 2. M.P. 166°–168° C. (methanol).

EXAMPLE 12

6-Methyl-4-(2'-morpholinoethoxy)-3-phenyl-coumarin

This compound is prepared as described in Example 8 from 19.4 g. (0.077 mol) of 6-methyl-4-hydroxy-3-phenyl-coumarin and 16.1 g. (0.1 mol) of 2-morpholino-2-chlorethane. Weight 21.7 g.; yield 77% (theoretical yield 28.2 g.). M.P. 96° C.

Maleate

Obtained as indicated in Example 2. M.P. 157°–159° C. (methanol).

EXAMPLE 13

3-Phenyl-4-(2'-morpholinoethoxy)-[1-2-b]-cycloheptano-(2H)-pyran-2-one

STAGE A:
3-Phenyl-4-hydroxy-[1-2-b]-cycloheptano-(2H)-pyran-2-one

This compound is prepared by thermal condensation of cycloheptanone and ethyl phenyl malonate in diphenyl ether. M.P. 146° C. Yield 50%.

STAGE B:
3-Phenyl-4-(2'-morpholinoethoxy)-[1-2-b]-cycloheptano-(2H)-pyran-2-one

This compound is prepared according to the method of Example 9, from 12 g. (0.047 mol) of 3-phenyl-4- hydroxy-[1-2-b]-cycloheptano-(2H)-pyran-2-one. The product is a clear oil which cannot be crystallised.

Acid oxalate

Obtained as indicated in Example 3. M.P. 165°–166° C.

EXAMPLE 14

4-(2'-Morpholinoethoxy)-3-phenyl-5,6,7,8-tetrahydrocoumarin

The preparation is carried out in the following stages.

STAGE A:
4-Hydroxy-3-phenyl-5,6,7,8-tetrahydro-coumarin 29.4 g. (0.3 mol) of cyclohexanone, 70.9 g. (0.3 mol) of diethyl phenyl malonate and 120 g. of diphenyl ether are progressively heated to 225° C. The temperature is then kept between 225° and 260° C. for 10 hours, with distillation of the ethyl alcohol which has formed. The medium is then cooled and thereafter diluted with 100 ml. of diisopropyl ether. The solid as obtained is filtered and it is recrystallised from ethanol. M.P. 168° C.; weight 39.5 g.; yield 54.2% (theoretical yield 72.7 g.).

STAGE B:
4-(2'-Morpholinoethoxy)-3-phenyl-5,6,7,8-tetrahydrocoumarin

The desired product is prepared according to the method of Example 9 from 14.5 g. (0.06 mol) of 3-phenyl-4-hydroxy-5,6,7,8-tetrahydro-coumarin and 11.7 g. (0.078 mol) of 2-morpholino-2-chlorethane. M.P. 115° C. (ethanol); weight 15.1 g. (yield 71%, theoretical yield 21.3 g.).

Oxalate

Obtained as indicated in Example 3. M.P. 179°–181° C. (methanol).

EXAMPLE 15

3-(3'-Chlorophenyl)-4-(2''-morpholinoethoxy)-coumarin

This compound is prepared according to the method of Example 8 from 6 g. (0.024 mol) of 3-(3'-chlorophenyl)-4-hydroxy-coumarin and 4.8 g. (0.032 mol) of 2-morpholino-1-chlorethane. 7 g. of an oil which cannot be crystallised are obtained. Yield 75% (theoretical yield 9.25 g.).

Maleate

Obtained as in Example 2, but operating in ethanol. M.P. 143°–146° C. (ethanol).

EXAMPLE 16

4-(3'-Morpholinopropoxy)-3-phenyl-coumarin

This compound is obtained by the method indicated in Example 8, from 14.3 g. (0.06 mol) of 4-hydroxy-3-phenyl-coumarin and 15.6 g. (0.078 mol) of 3-morpholino-1-chloropropane hydrochloride. 15.6 g. of a white solid are isolated. Yield 71% (theoretical yield 21.9 g.); M.P. 82° C. (isopropanol).

Hydrochloride

Obtained as indicated in Example 13. M.P. 173°–177° C. (methanol).

EXAMPLE 17

4-[(1'-Methyl-2'-piperidinyl)-methoxy]-3-phenyl-coumarin

This compound is prepared according to the method of Example 8 from 23.8 g. (0.1 mol) of 4-hydroxy-3-phenyl-coumarin and 19.2 g. (0.13 mol) of 2-chloromethyl-1-methyl-piperidine. 19.4 g. of a white solid are obtained. M.P. 108° C. (diisopropyl ether); yield 55.5% (theoretical yield 34.9 g.).

EXAMPLE 18

4-(3'-Morpholino-2'-methylpropoxy)-3-phenyl-(1-2-b)-cycloheptane-(2H)-pyran-2-one This compound is prepared according to the method of Example 13 from 12 g. (0.047 mol) of 4-hydroxy-3-phenyl-(1-2-b)-cycloheptano-(2H)-pyran-2-one and 10.7 g. (0.061 mol) of 3-morpholino-2-methyl-1-chloropropane. The product is a clear oil which cannot be crystallised.

Acid oxalate

Prepared according to Example 3, a white solid is isolated. M.P. 171°–173° C.

EXAMPLE 19

4-(3'-Morpholino-2'-methylpropoxy)-3-phenyl-coumarin

This compound is prepared according to the method of Example 8 from 14.3 g. (0.06 mol) of 4-hydroxy-3-phenyl-coumarin and 16.7 g. (0.078 mol) of 3-morpholino-2-methyl-1-chloropropane hydrochloride. After recrystallisation from ethanol, 18.8 g. are obtained. Yield 82.5% (theoretical yield 22.8 g.); M.P. 113° C.

Hydrochloride

M.P. 186°–189° C. (isopropanol).

EXAMPLE 20

7-Methoxy-4-(2'-morpholinoethoxy)-3-phenyl-coumarin

This compound is prepared according to the method described in Example 8 from 24.2 g. (0.09 mol) of 3-phenyl-4-hydroxy-7-methoxy-coumarin and 17.5 g. (0.117 mol) of 2-morpholino-1-chlorethane. After recrystallisation from a mixture of diisopropyl ether and ethyl acetate (70–30), 24.3 g. of a white solid are obtained. M.P. 95°–96° C.; yield 70.8% (theoretical yield 34.3 g.).

Hydrochloride

Obtained in the manner indicated in Example 13, but using methanol as solvent. M.P. 192°–194° C. (methanol).

EXAMPLE 21

8-Methoxy-4-(2'-morpholinoethoxy)-3-phenyl-coumarin

This compound is prepared according to the method of Example 8 from 45.6 g. (0.17 mol) of 3-phenyl-4-hydroxy-8-methoxy-coumarin and 30.5 g. (0.24 mol) of 2-morpholino-1-chlorethane. After recrystallisation from isopropanol, 48 g. are isolated; M.P. 90°–91° C. Yield 74% (theoretical yield 65.0 g.).

Hydrochloride

Obtained in the manner indicated in Example 13. M.P. 186°–189° C. (methanol).

Maleate

Obtained in the manner indicated in Example 2. M.P. 126°–130° C. (methanol).

EXAMPLE 22

4-(2'-Morpholinoethoxy)-3-phenyl-6-methoxy-coumarin

This compound is obtained according to the method of Example 8 from 12.1 g. (0.045 mol) of 6-methoxy-3-phenyl-4-hydroxy-coumarin and 10.9 g. (0.057 mol) of 2-morpholino-1-chlorethane. After recrystallisation from isopropanol, 11.3 g. of a beige-coloured solid are obtained. M.P. 118° C.; yield 67.5% (theoretical yield 16.7 g.).

Oxalate

Prepared by the method of Example 3. M.P. 183°–184° C. (methanol-water: 90–10).

EXAMPLE 23

Bis-4,5-(2'-morpholinoethoxy)-3-phenyl-coumarin (a) Isolation of 4,5-dihydroxy-3-phenyl-coumarin 165 g. (1.5 mol) of resorcinol and 354 g. (1.5 mol) of ethyl phenyl malonate are condensed at 235° C. for 2½ hours in 600 g. of diphenyl ether. After cooling to 70° C. and dilution with diisopropyl ether, 296 g. of a product are obtained which melts at 256°–265° C. It is recrystallised from 8 liters of dioxane and is left to return in 78 hours to room temperature. It is recovered and dried. Weight 201.5 g.; yield 52.8% (theoretical yield 381 g.). M.P. 264°–266° C.

As the 4,7-dihydroxy-3-phenyl-coumarin isomer may also be formed during the reaction, a thin-film chromatographic separation of the products obtained is carried out:

silica gel plate GF 254
deposit 100
eluting agent: methyl ethyl ketone

The product only gives a single spot with an absence of a spot at the Rf corresponding to the 4,7-dihydroxy isomer (the latter having been prepared in a one-way manner by demethylation of the 7-methoxy-4-hydroxy-3-phenyl coumarin). The presence of 4,7-dihydroxy-3-phenyl-coumarin has been shown in the recrystallisation mother liquors.

(b) Bis-4,5-(2'-morpholinoethoxy)-3-phenyl-coumarin

The desired product is prepared by the procedure described in the Example from 508 g. (2 mols) of 3-phenyl-4,5-dihydroxy-coumarin and 780 g. (5.2 mols) of 2-morpholino-1-chlorethane. After recrystallisation from ethanol, 568.5 g. of a white solid are obtained. M.P. 117° C.; yield 59.4% (theoretical yield 960 g.)

Maleate

M.P. 118°–123° C. (ethanol).

EXAMPLE 24

Bis-4,5-(3'-morpholinopropoxy)-3-phenyl-coumarin

This compound is obtained according to the method of Example 8, from 9.77 g. (0.034 mol) of 4,5-dihydroxy-3-phenyl-coumarin and 20 g. (0.1 mol) of 3-morpholino-1-chloropropane hydrochloride. After recrystallisation from isopropanol, 9.3 g. of a white solid are obtained; M.P. 90° C.; yield 48.5% (theoretical yield 19.2 g.).

Dioxalate

M.P. 191°–193° C. (methanol).

EXAMPLE 25

Bis-4,8-(2'-morpholinoethoxy)-3-phenyl-coumarin.

STAGE A. 4,8-Dihydroxy-3-phenyl-coumarin.

37.6 g. (0.14 mol) of 8-methoxy-4-hydroxy-3-phenyl-coumarin are brought to reflux for 1 hour in a mixture of 750 ml. of 62% hydrobromic acid, 375 ml. of glacial acetic acid and 375 ml. of acetic anhydride. The mixture is poured on to 5.3 kg. of ice, filtered and dried. 25.3 g. of a solid are obtained, which is recrystallised from a mixture of dioxane and diisopropyl ether (50:50). Weight 13 g., yield 38.1% (theoretical yield 34.2 g.); M.P. 220° C.

STAGE B.

Bis-4,8-(2'-morpholinoethoxy)-3-phenyl-coumarin.

This is obtained according to the method of Example 8, from 10.2 g. (0.04 mol) of 4,8-dihydroxy-3-phenyl-coumarin and 18.6 g. (0.104 mol) of 2-morpholino-1-chlorethane. After recrystallisation from ethanol, a white solid is isolated. M.P. 103° C.; weight 7.9 g.; yield 41.2% (theoretical yield 19.2 g.).

Dioxalate

M.P. 122°–124° C. (methanol).

EXAMPLE 26

Bis-4,6-(2'-morpholinoethoxy)-3-phenyl-coumarin.

STAGE A. 4,6-Dihydroxy-3-phenyl-coumarin.

Prepared in the manner described in Example 25, Stage A, from 37.6 g. (0.14 mol) of 6-methoxy-4-hydroxy-3-phenyl-coumarin, 375 ml. of glacial acetic acid, 750 ml. of 62% hydrobromic acid and 375 ml. of acetic anhydride. Weight 12.2 g.; yield 33.7% (theoretical yield 35.6 g.); M.P. 261°–263° C. (dioxane-diisopropyl ether: 50-50).

STAGE B.

Bis-4,6-(2'-morpholinoethoxy)-3-phenyl-coumarin.

10.2 g. (0.04 mol) of 4,6-dihydroxy-3-phenyl-coumarin are treated as indicated in Example 8 with 15.6 g. (0.104 mol) of 2-morpholino-1-chloropropane. After evaporating off the chloroform, 17 g. of an oil are isolated, which cannot be crystallised. Yield 88% (theoretical yield 19.2 g.).

Dihydrochloride

M.P. 159°–162° C. (ethanol).

EXAMPLE 27

4-[3-(4''-Methyl-1''-piperazinyl)-propoxy]-3-phenyl-coumarin.

Prepared in the manner described in Example 8, using 11.9 g. (0.05 mol) of N-methyl-N'-(γ-chloropropyl)-piperazine. After evaporation of the chloroform, 13.8 g. of an oil are obtained, which cannot be crystallised. Yield 88% (theoretical yield 18.6 g.).

Dihydrochloride

M.P. 116°–126° C. (methanol).

EXAMPLE 28

Bis-4,7-(2'-morpholinoethoxy)-3-phenyl-coumarin.

10.2 g. (0.04 mol) of 4,7-dihydroxy-3-phenyl-coumarin (prepared by demethylation of the 7-methoxy-4-hydroxy-3-phenyl-coumarin in the manner described in Example 25, Stage A) are treated by the method described in Example 8 with 15.6 g. (0.104 mol) of 2-morpholino-1-chlorethane. After evaporation of the chloroform, an oil is obtained which cannot be crystallised. Weight 15 g.; yield 78% (theoretical yield 19.2 g.).

Dioxalate

M.P. 169°–170° C. (methanol).

EXAMPLE 29

4-(3'-Isopropylamino-2'-hydroxypropoxy)-3-phenyl-coumarin.

STAGE A.

4-[(2',3')-epoxypropoxy]-3-phenyl-coumarin.

31 g. (0.13 mol) of 3-phenyl-4-hydroxy-coumarin, 21.5 g. (0.156 mol) of dry potassium carbonate and 18.1 g (0.195 mol) of epichlorohydrin are refluxed for 14 hours in 140 ml. of methyl isobutyl ketone. The substance is filtered while hot and the filtrate is evaporated under vacuum. The pasty residue (22 g.) is recrystallised from methanol and 12.2 g. of a white solid are obtained. Yield 31.8% (theoretical yield 38.3 g.); M.P. 134° C.

STAGE B.

4-(3'-Isopropylamino-2'-hydroxypropoxy)-3-phenyl-coumarin.

11.8 g. (0.04 mol) of 4-(2'-3'-epoxypropoxy)-3-phenyl-coumarin are solubilised in 170 ml. of isopropanol. 9.4 g. (0.16 mol) of isopropyl amine are then added at ambient temperature. The solution is then refluxed for 3 hours. The solvents and the excess amine are evaporated under vacuum and 11.5 g. of an oil are obtained, which cannot be crystallised. Yield 81.7% (theoretical yield 14.1 g.).

Hydrochloride

M.P. 191°–194° C. (methanol - ether: 50 - 50).

EXAMPLE 30

4-(2'-Morpholinoethoxy)-5-hydroxy-3-phenyl-coumarin.

76.3 g. (0.3 mol) of 4,5-dihydroxy-3-phenyl-coumarin (Example 23a), 25.2 g. (0.3 mol) of sodium bicarbonate, 3 g. of potassium iodide and 800 ml. of methyl isobutyl ketone are brought over one hour to 80° C. The mixture is then cooled to 60° C., whereafter 48.4 g. (0.324 mol) of 2-morpholino-1-chlorethane are added dropwise and the temperature is brought over 8 hours to 100° C. It is then left at room temperature for one night and filtered. The precipitate obtained is taken up in 1 liter of chloroform. The light, insoluble substance obtained is filtered and the chloroform is evaporated under vacuum. The residue obtained is recrystallised from 700 ml. of methyl isobutyl ketone. 50 g. of a white product are isolated. M.P. 206° C.; yield 44.5% (theoretical yield 110.2 g.).

As bis-4,5-(2'-morpholinoethoxy)-3-phenyl-coumarin (Example 23) is also capable of forming during the reaction, the product obtained is treated to a thin-film chromatographic separation:

silica gel plate GF 254
deposit: 100
eluant:
  ethyl acetate: 5 parts
  methyl ethyl ketone: 3 parts
  formic acid: 1 part
  water: 1 part Hydrochloride M.P. 178°–180° C. (methanol).

EXAMPLE 31

5-Methoxy-4-(2'-morpholinoethoxy)-3-phenyl-coumarin.

18.4 g. (0.05 mol) of 4-(2'-morpholinoethoxy)-5-hydroxy-3-phenyl coumarin (Example 30), 9.7 g. (0.07 mol) of potassium carbonate, 0.5 g. of potassium iodide and 250 ml. of methyl isobutyl ketone are brought over one hour to 80° C. The temperature is then brought to 60° C. and 7.6 g. (0.06 mol) of freshly distilled dimethyl sulphate are added dropwise in 20 minutes. Refluxing takes place for 8 hours and, after cooling, filtering is carried out. The filtrate is evaporated under vacuum and then, after washing with sodium bicarbonate and then water, and extraction with chloroform, there are obtained, after evaporation, 4.8 g. of an oil which cannot be crystallised. Yield 25.2% (theoretical yield 19.1 g.).

Oxalate

M.P. 181°–185° C. (methanol).

EXAMPLE 32

4-(3'-Morpholino-2'-hydroxypropoxy)-3-phenyl-coumarin.

Prepared as indicated in Stage B of Example 29 from 17.6 g. (0.06 mol) of 4-(2',3'-epoxypropoxy)-3-phenyl-coumarin (Example 29, Stage A) and 22 g. (0.25 mol) of morpholine. After evaporation, 18 g. of an oil are obtained which cannot be crystallised. Yield 79% (theoretical yield 22.8 g.).

Hydrochloride

M.P. 109°–211° C. (methanol - water).

EXAMPLE 33

4-(2'-Morpholinoethoxy)-7-hydroxy-3-phenyl-coumarin.

Following the method of Example 30, 30.5 g. (0.12 mol) of 3-phenyl-4,7-dihydroxy-coumarin are treated with 19.5 g. (0.13 mol) of 2-morpholino-1-chloroethane. 34 g. of an oil are obtained, which cannot be crystallised. Yield 77.6% (theoretical yield 44.7 g.).

Hydrochloride

M.P. 206°–236° C. (methanol - water).

EXAMPLE 34

8-Methoxy-4-(2'-morpholinoethoxy)-3-phenyl-coumarin.

As in Example 8, 45.6 g. (0.17 mol) of 8-methoxy-4-hydroxy-3-phenyl-coumarin are treated with 30.5 g. (0.20 mol) of 2-morpholino-1-chlorethane. After evaporation of the chloroform and recrystallisation from isopropanol, 48 g. of a beige-coloured solid are obtained. M.P. 90°–91° C.; yield 76% (theoretical yield 63 g.).

Maleate

M.P. 126°–130° C. (ethanol)

Hydrochloride

M.P. 186°–189° C. (methanol).

EXAMPLE 35

8-Hydroxy-4-(2'-morpholinoethoxy)-3-phenyl-coumarin.

Prepared as described in Example 30 from 45.9 g. (0.18 mol) of 3-phenyl-4,8-dihydroxy-coumarin and 31.5 g. (0.21 mol) of 2-morpholino-1-chloroethane. After recrystallisation from ethane, 39.8 g. of a white substance are obtained; M.P. 190°–191° C. Yield 60.2% (theoretical yield 66 g.).

Hydrochloride, monohydrate

M.P. 200°–208° C. (methanol - water: 5-1).

EXAMPLE 36

4-(2'-Morpholinoethoxy)-3-(4'-methoxyphenyl)-coumarin.

Obtained according to the method of Example 8, from 12.1 g. (0.045 mol) of 3-(4'-methoxyphenyl)-4-hydroxy-coumarin and 8.7 g. (0.058 mol) of 2-morpholino-1-chlorethane. After recrystallisation from ethanol, there are obtained 14.7 g. of a beige product; M.P. 104° C. Yield 82.5% (theoretical yield 17.1 g.).

Hydrochloride

M.P. 167°–170° C. (ethanol)

EXAMPLE 37

4-(3'-Piperidino-2'-hydroxypropoxy)-3-phenyl-coumarin.

Prepared according to the method of Example 29, Stage B, from 11.8 g. (0.04 mol) of 3-phenyl-4-(2',3'-epoxypropoxy)coumarin (Example 29, Stage A) and 13.6 g. (0.16 mol) of piperidine. After evaporation of the solvents, there are obtained 10.5 g. of an oil which cannot be crystallised. Yield 69% (theoretical yield 15.2 g.).

Hydrochloride

M.P. 202°–204° C. (methanol).

EXAMPLE 38

4-(3'-Pyrrolidino-2'-hydroxypropoxy)-3-phenyl-coumarin.

Prepared according to the method of Example 29, Stage B, from 11.8 g. (0.04 mol) of 3-phenyl-4-(2',3'-epoxypropoxy)coumarin (Example 29, Stage A) and 11.4 g. (0.16 mol) of pyrrolidine. 9.6 g. of an oil are obtained, which cannot be crystallised. Yield 65% (theoretical yield 14.6 g.).

Hydrochloride

M.P. 204°–207° C. (methanol).

EXAMPLE 39

3-Phenyl-4-[2'-(3'',4'',5''-trimethoxybenzoyloxy)-3'-morpholinopropoxy]-coumarin.

14.2 g. (0.034 mol) of 4-(3'-morpholino-2'-hydroxypropoxy)-3-phenyl-coumarin hydrochloride (Example 32) are placed in 130 ml. of chloroform containing 3.4 g. (0.034 mol) of triethylamine. A solution of 7.83 g. (0.034 mol) of 3,4,5-trimethoxy-benzoyl chloride in 20 ml. of chloroform are then added in 2½ hours. The mixture is then brought over 2 hours to 40°–50° C. Cooling takes place, the insoluble substance is filtered off, the filtrate is washed with a sodium bicarbonate solution and dried over sodium sulphate. The solvent is evaporated under vacuum and there are obtained 14.3 g. of an oil which cannot be crystallised. Yield 73.4% (theoretical yield 19.5 g.).

Hydrochloride

M.P. 185°–189° C. (methanol).

EXAMPLE 40

3-Benzyl-4-(2'-morpholinoethoxy)-coumarin.

Prepared as indicated in Example 8, from 13.7 g. (0.54 mol) of 3-benzyl-4-hydroxy-coumarin and 10.6 g. (0.071 mol) of 2-morpholino-1-chlorethane. After evaporation of the chloroform, there are obtained 17 g. of an oil which cannot be crystallised. Yield 88.5% (theoretical yield 19.2 g.).

Oxalate

M.P. 93°–100° C. (acetone).

EXAMPLE 41

4-(2'-Morpholinoethoxy)-3-phenyl-6-tert.-butyl-5,6,7,8-tetrahydro-coumarin.

STAGE A.

4-Hydroxy-3-phenyl-6-tert.butyl-5,6,7,8-tetrahydrocoumarin.

Prepared according to Example 14, Stage A, from 30.85 g. (0.2 mol) of 4-tert.butyl-cyclohexane and 47.3 g. (0.2 mol) of diethyl phenyl malonate. After recrystallisation from ethyl acetate, 28.8 g. of a white substance are obtained. M.P. 195° C., yield 48.3% (theoretical yield 59.6 g.).

STAGE B.

4-(2'-Morpholinoethoxy)-3-phenyl-6-tert.-butyl-5,6,7,8-tetrahydro-coumarin.

Obtained according to Example 14, Stage B, by treating 14.2 g. (0.05 mol) of 4-hydroxy-3-phenyl-6-tert.butyl-5,6,7,8-tetrahydro-coumarin with 9.7 g. (0.065 mol) of 2-morpholino-1-chlorethane. After evaporation of the chloroform, 17 g. of an oil are obtained, which cannot be crystallised. Yield 84.6% (theoretical yield 20.35 g.).

Oxalate

M.P. 196° C. (ethanol).

EXAMPLE 42

4-(2'-Morpholinoethoxy)-3-phenyl-[1-2-b]-cyclododeceno-[2H]-pyran-2-one

STAGE A.

4-Hydroxy-3-phenyl-[1-2-b]-cyclododeceno-[2H]-pyran-2-one

Prepared as indicated in Example 14, Stage A, from 36.4 g. (0.2 mol) of cyclododecanone and 47.3 g. (0.2 mol) of diethyl phenyl malonate. After recrystallisation from an ethyl acetate hexane mixture, 31.2 g. of a pale yellow solid are obtained. M.P. 140° C. Yield 43.8% (theoretical yield 65.2 g.).

STAGE B.
4-(2'-Morpholinoethoxy)-3-phenyl-[1-2-b]-cyclododeceno-[2H]-pyran-2-one.

Obtained according to Example 14, Stage B, from 13 g. (0.04 mol) of 4-hydroxy-3-phenyl-[1-2-b]-cyclododeceno-[2H]-pyran-2-one and 7.75 g. (0.032 mol) of 2-morpholino-1-chlorethane. By recrystallisation from diisopropyl ether, 6.1 g. of a white substance are obtained. M.P. 109°–112° C. Yield 35% (theoretical yield 17.2 g.).

EXAMPLE 43
4-(2'-Diethylaminoethoxy)-3-phenyl-5,6,7,8-tetrahydrocoumarin.

Prepared as indicated in Example 14, Stage B, from 12.1 g. (0.05 mol) of 4-hydroxy-3-phenyl-5,6,7,8-tetrahydrocoumarin (Example 14, Stage A) and 8.8 g. (0.065 mol) of 2-diethylamino-1-chloroethane. 13.2 g. of an oil are obtained, which cannot be crystallised. Yield 68.7% (theoretical yield 19.2 g.).

Oxalate
M.P. 153°–154° C. (ethanol).

EXAMPLE 44
4-(2'-Morpholinoethoxy)-3-phenyl-5,6-dihydro-[h]-benzocoumarin.

STAGE A.
4-Hydroxy-3-phenyl-5,6-dihydro-[h]-benzocoumarin.

Obtained according to Example 14, Stage A, from 29.2 g. (0.2 mol) of α-tetralone and 47.2 g. (0.2 mol) of diethyl phenyl malonate. 32.1 g. are obtained. M.P. 204° C. Yield 55.5% (theoretical yield 58 g.).

STAGE B.
4-(2'-Morpholinoethoxy)-3-phenyl-5,6-dihydro-[h]-benzocoumarin.

Prepared as in Example 14, Stage B, from 14.5 g. (0.05 mol) of 4-hydroxy-3-phenyl-5,6-dihydro[h]-benzocoumarin and 9.7 g. (0.065 mol) of 2-morpholino-1-chlorethane. Obtained: 11.6 g. M.P. 126° C. (isopropanol), yield 58% (theoretical yield 20.15 g.).

Hydrochloride
M.P. 183°–184° C. (ethanol -diisopropyl ether).

EXAMPLE 45
4-(2'-Morpholinoethoxy)-3,9-diphenyl-[2-1-b]-indeno-[2H]-pyran-2-one

STAGE A.
4-Hydroxy-3,9-diphenyl-[2-1-b]-indeno-[2H]-pyran-2-one

Prepared as in Example 14, Stage A, from 41.6 g. (0.2 mol) of 3-phenylindan-1-one and 47.2 g. (0.2 mol) of ethyl phenyl malonate. A paste is obtained which, taken up in ethyl acetate, gives a clear chestnut-coloured solid: weight 9.1 g.; M.P. 235° C. Yield 13% (theoretical yield 70.4 g.).

STAGE B.
4-(2'-Morpholinoethoxy)-3,9-diphenyl-[2-1-b]-indeno-[2H]-pyran-2-one Obtained by causing the reaction, in accordance with Example 14, Stage B, of 14.9 g. (0.042 mol) of 4-hydroxy-3,9-diphenyl-[2-1-b]-indeno-[2H]-pyran-2-one and 8.15 g. (0.054 mol) of 2-morpholino-1-chlorethane. After recrystallisation from ethyl acetate, 11.1 g. of a yellow solid are obtained. M.P. 198° C., yield 57% (theoretical yield 19.5 g.).

Hydrochloride
M.P. 201°–202° C. (ethanol)

Methanesulphonate
M.P. 186°–188° C. (ethanol-diisopropyl ether)

EXAMPLE 46
4-(3'-Morpholino-2'-methylpropoxy)-3-phenyl-5,6,7,8-tetrahydrocoumarin.

Prepared as indicated in Example 14, Stage B, from 29 g. (0.12 mol) of 4-hydroxy-3-phenyl-5,6,7,8-tetrahydrocoumarin and 27.3 g. (0.156 mol) of 3-morpholino-2-methyl-2-chloropropane. 38.2 g. of an oil which cannot be crystallised are obtained. Yield 83.5% (theoretical yield 45.6 g.).

Oxalate
M.P. 175°–177° C. (methanol)

EXAMPLE 47
4-(3'-Morpholinopropoxy)-3-phenyl-5,6,7,8-tetrahydrocoumarin.

Obtained by causing the reaction, as indicated in Example 14, Stage B, of 14.5 g. (0.06 mol) of 4-hydroxy-3-phenyl-5,6,7,8-tetrahydrocoumarin with 15.6 g. (0.078 mol) of 3-morpholino-1-chloropropane. 10.1 g. of a paste which cannot be crystallised are isolated. Yield 45.7% (theoretical yield 22.1 g.).

Oxalate
M.P. 183°–184° C. (methanol).

EXAMPLE 48
4-(3'-Isopropylamino-2'-hydroxypropoxy)-3-phenyl-5,6,7,8-tetrahydrocoumarin.

STAGE A.
4-(2',3'-Epoxypropoxy)-3-phenyl-5,6,7,8-tetrahydrocoumarin.

As in Example 29, Stage A, 42 g. (0.173 mol) of 3-phenyl-4-hydroxy-5,6,7,8-tetrahydrocoumarin are reacted with 18.1 g. (0.26 mol) of 1-chloro-2,3-epoxypropane. 41 g. of an oil which cannot be crystallised are obtained. Yield 80.5% (theoretical yield 51 g.).

STAGE B.
4-(3'-Iospropylamino-2'-hydroxypropoxy)-3-phenyl-5,6,7,8-tetrahydrocoumarin.

15 g. (0.051 mol) of 4-(2',3'-epoxypropoxy)-3-phenyl-5,6,7,8-tetrahydrocoumarin are treated as in Example 29, Stage B, with 30 g. (0.51 mol) of isopropylamine. After evaporation of the solvents, 12.6 g. of an oil which cannot be crystallised are obtained. Yield 69.2% (theoretical yield 18.2 g.).

Oxalate
M.P. 189°–190° C. (methanol)

EXAMPLE 49

4-(3'-Dibutylaminopropoxy)-3-phenyl-5,6,7,8-tetrahydrocoumarin

As in Example 14, Stage B, 14.5 g. (0.06 mol) of 4-hydroxy-3-phenyl-5,6,7,8-tetrahydrocoumarin are caused to react with 16.2 g. (0.078 mol) of 1-chloro-3-dibutylaminopropane. 19.8 g. of an oil which cannot be crystallised are obtained. Yield 80.5% (theoretical yield 24.6 g.).

Oxalate

M.P. 74°–77° C. (acetone).

EXAMPLE 50

4-(2'-Morpholinoethoxy)-3,8-diphenyl-coumarin

STAGE A. 4-Hydroxy-3,8-diphenyl-coumarin

A mixture of 102 g. (0.6 mol) of 2-phenyl-phenol and 141.8 g. (0.6 mol) of diethyl phenyl malonate is brought over 4½ hours to 250°–260° C. After cooling, the solid is recrystallised from 1.7 liters of ethanol. 94.3 g. are obtained. M.P. 211° C. Yield 50% (theoretical yield 188.8 g.).

STAGE B.
4-(2'-Morpholinoethoxy)-3,8-diphenyl-coumarin 15.7 g. (0.05 mol) of 4-hydroxy-3,8-diphenyl-coumarin are treated, as in Example 8, with 9.7 g. (0.065 mol) of 1-chloro-2-morpholinoethane. After recrystallisation from isopropanol, 16 g. are obtained. M.P. 106°–108° C. Yield 75% (theoretical yield 21.3 g.).

EXAMPLE 51

4-(3'-Morpholino-2'-methylpropoxy)-3-phenyl[1-2-b]-cyclooctano-(2H)-pyran-2-one

STAGE A.
4-Hydroxy-3-phenyl-[1-2-b]-cyclooctano-(2H)-pyran-2-one

Prepared as in Example 14, Stage A, by thermal condensation in diphenyl ether between cyclooctanone and ethyl phenyl malonate. M.P. 154° C. Yield 50%.

STAGE B.
4-(3'-Morpholino-2'-methylpropoxy)-3-phenyl-[1-2-b]-cyclooctano-(2H)-pyran-2-one Prepared according to the method of Example 13. The product is an oil which cannot be crystallised.

Acid oxalate

Prepared according to the method of Example 3, a white solid is isolated. M.P. 159°–160° C.

EXAMPLE 52

4-(3'-Morpholino-2-methylpropoxy)-3-phenyl-[1-2-b]-cyclododeceno-(2H)-pyran-2-one Prepared according to the method of Example 42, Stage B, by alkylation of 4-hydroxy-3-phenyl-[1-2-b]-cyclododeceno-(2H)-pyran-2-one with 1-chloro-2-methyl-3-morpholino-propane. An oil which cannot be crystallised is isolated.

Acid oxalate

M.P. 72° C. (pasty) (acetone)

EXAMPLE 53

4-(3'-Morpholino-2'-methylpropoxy)-3-phenyl-8-hydroxy-coumarin

Prepared according to the method of Example 30 by alkylation of 4,8-dihydroxy-3-phenyl-coumarin by 1-chloro-2-methyl-3-morpholino-propane. After recrystallisation from isopropanol, a white solid is obtained with the melting point of 136° C. Yield 60.7%.

Hydrochloride

M.P. 208°–210° C. (methanol).

EXAMPLE 54

4-(3'-Morpholino-2-methylpropoxy)-3-phenyl-6-tert.butyl-5,6,7,8-tetrahydro-coumarin Prepared according to the method of Example 9 from 12.8 g. (0.043 mol) of 4-hydroxy-3-phenyl-6-tert.butyl-5,6,7,8-tetrahydro-coumarin and 10.7 g. (0.061 mol) of 3-morpholino-2-methyl-1-chloropropane. The product is a thick oil which cannot be crystallised.

Oxalate

Prepared according to the method of Example 3, a beige solid, m.p. 71° C. (ethyl acetate).

EXAMPLE 55

3,8-Diphenyl-4-(3'-morpholino-2'-methylpropoxy)-5,6,7,8-tetrahydro-coumarin

STAGE A.
3,8-Diphenyl-4-hydroxy-5,6,7,8-tetrahydrocoumarin

Prepared according to the method of Example 14, Stage A, by thermal condensation in diphenyl ether of 2-phenyl-cyclohexanone and ethyl phenyl malonate. M.P. 185° C. (Dipropyl ether/ethanol).

STAGE B.
3,8-Diphenyl-4-(3'-morpholino-2'-methylpropoxy)-5,6,7,8-tetrahydrocoumarin Prepared according to the method of Example 9 from 3,8-diphenyl-4-hydroxy-5,6,7,8-tetrahydrocoumarin and 1-chloro-2-methyl-3-morpholino-propane. A thick, brown oil is obtained which cannot be crystallised. Yield 35%.

Oxalate

Prepared according to the method of Example 3. M.P. 146°–148° C. (isopropanol).

EXAMPLE 56

4-(3'-Piperidino-2'-methylpropoxy)-3-phenyl-[1-2-b]-cycloocteno-[2H]-pyran-2-one Prepared according to the method of Example 13, by alkylation of 4-hydroxy-3-phenyl-[1-2-b]cyclooucteno-[2H]-pyran-2-one with 3-piperidino-2-methyl-1-chloropropane. By recrystallisation from hexane, a beige solid substance is obtained. Yield 51.7%. M.P. 98° C.

Oxalate

Prepared according to the method of Example 3. M.P. 150°–152° C. (isopropano-ethanol).

EXAMPLE 57

4-(3'-Piperidino-2'-methylpropoxy)-3-phenyl-5,6,7,8-tetrahydrocoumarin

Prepared according to the method of Example 13 by alkylation of 4-hydroxy-3-phenyl-5,6,7,8-tetrahydrocoumarin with 3-piperidino-2-methyl-1-chloropropane. A thick oil is obtained which cannot be crystallised. Yield 82%.

Oxalate

Prepared according to the method of Example 3. M.P. 177°–178° C. (ethyl acetate/methanol).

EXAMPLE 58

4-(3'-Piperidino-2'-hydroxypropoxy)-3-phenyl-5,6,7,8-tetrahydrocoumarin

Prepared according to the method of Example 29, Stage B, from 3-phenyl-4-(2',3'-epoxypropoxy)-5,6,7,8-tetrahydrocoumarin (Example 48, Stage A) and piperidine. An oil is obtained which cannot be crystallised. Yield 75%.

Oxalate

Prepared according to the method of Example 3. M.P. 166°–168° C. (acetone/methanol).

EXAMPLE 59

4-(3'-Morpholinobutoxy)-3-phenyl-coumarin

Prepared according to the method of Example 8 from 4-hydroxy-3-phenyl-coumarin and 3-morpholino-1-chlorobutane. An oil is obtained which cannot be crystallised. Yield 72.5%.

Hydrochloride

Obtained by solubilising the oil in isopropanol and by fixing the theoretical quantity of hydrochloric acid gas. M.P. 191°–192° C. (ethanol).

EXAMPLE 60

4-(3'-Piperidino-2'-methylpropoxy)-3-phenyl-coumarin

Prepared from 3-phenyl-4-hydroxy-coumarin and 3-piperidino-2-methyl-1-chloropropane, according to the method of Example 8. A light yellow solid is obtained. M.P. 86°–87° C. (hexane). Yield 77.5%.

Hydrochloride

Obtained according to the method of Example 59. M.P. 172°–175° C. (isopropanol).

EXAMPLE 61

4-(3'-Morpholino-2',2'-dimethylpropoxy)-3-phenyl-coumarin

Prepared according to the method of Example 8 from 4-hydroxy-3-phenyl-coumarin and 3-morpholino-2,2-dimethyl-1-chloropropane. By recrystallisation from ethanol, a solid melting at 167° C. is obtained. Yield 87.2%.

Hydrochloride

Prepared by solubilising the base in chloroform and by fixing the theoretical quantity of hydrochloric acid gas. M.P. 181°–186° C. (ethanol).

EXAMPLE 62

8-Chloro-4-(3'-morpholino-2'-methylpropoxy)-3-phenyl-coumarin

STAGE A. 8-Chloro-4-hydroxy-3-phenyl-coumarin

Prepared by thermal condensation between 2-chlorophenol and ethyl phenyl malonate. M.P. 245° C. (dioxane).

STAGE B.

8-Chloro-4-(3'-morpholino-2'-methylpropoxy)-3-phenylcoumarin

Prepared by alkylation of 8-chloro-4-hydroxy-3-phenylcoumarin by 3-morpholino-2-methyl-1-chloropropane, in accordance with the method of Example 8. By recrystallisation from ethanol, a solid melting at 120°–122° C. is obtained. Yield 69%.

Hydrochloride

Prepared by solubilising the base in ethanol and by fixing the theoretical quantity of hydrochloric acid gas and then diluting with ether. M.P. 182°–184° C. (ethanol).

EXAMPLE 63

4-(3'-Morpholino-2'-methylpropoxy)-3,8-diphenyl-coumarin

Prepared according to the method of Example 8, by alkylation of 4-hydroxy-3,8-diphenyl-coumarin with 3-morpholino-2-methyl-1-chloropropane. After recrystallisation from ethanol, a solid melting at 120°–121° C. is obtained. Yield 69.1%.

Hydrochloride

Prepared by solubilising the base in an ethanol/ether mixture and by fixing the theoretical quantity of hydrochloric acid gas. M.P. 190°–193° C. (methanol/water).

EXAMPLE 64

4-(3'-Morpholino-2'-methylpropoxy)-3-phenyl-8-methyl-coumarin

Prepared according to the method of Example 8 from 4-hydroxy-8-methyl-3-phenyl-coumarin and 3-morpholino-2-methyl-1-chloropropane. An oil is obtained which cannot be crystallised. Yield 65%.

Hydrochloride

Prepared by solubilising the base in ether and by fixing the theoretical quantity of hydrochloric acid gas. M.P. 181°–183° C. (acetone/methanol).

EXAMPLE 65

4-(3'-Diethylamino-2'-propyloxy)-3-phenyl-5,6,7,8-tetrahydrocoumarin

Prepared according to the method of Example 9 from 4-hydroxy-3-phenyl-5,6,7,8-tetrahydro-coumarin and 1-diethylamino-2-chloropropane. After treatment with hexane, a beige-coloured solid is obtained. Yield 62%. M.P. 78° C.

Oxalate

Prepared by the method of Example 3. M.P. 137°–139° C. (Dipropyl ether/ethanol).

EXAMPLE 66

4-(4''-Methyl-3'-piperazinyl-2'-methylpropoxy)-3-phenyl-5,6,7,8-tetrahydro-coumarin Prepared according to the method of Example 9 from 4-hydroxy-3-phenyl-5,6,7,8-tetrahydrocoumarin and 3-[4'-methylpiperazinyl]-2-methyl-1-chloropropane. An oil is obtained which cannot be crystallised. Yield 55%.

Dioxalate

Prepared according to the method of Example 3. M.P. 181°–192° C. (acetone/water).

EXAMPLE 67

4-(3'-Morpholino-2'-hydroxypropoxy)-3-phenyl-5,6,7,8-tetrahydrocoumarin

A solution of 4-hydroxy-3-phenyl-5,6,7,8-tetrahydrocoumarin and 3-morpholino-1,2-epoxypropane in methyl isobutyl ketone is brought under reflux for 8 hours. Evaporation is carried out under vacuum and the residue is taken up by a 5% solution of sodium bicarbonate and kept for 15 minutes at reflux. After cooling, extraction is carried out with chloroform, drying takes place on sodium sulphate and the chloroform is evaporated. An oil is obtained which cannot be crystallised. Yield 77%.

Oxalate

Prepared according to the method of Example 3. M.P. 177°–178° C. (acetone/water).

EXAMPLE 68

4-(3'-Dibutylamino-2'-hydroxypropoxy)-3-phenyl-coumarin

Prepared according to the method of Example 29, Stage B, from 3-phenyl-4-(2',3'-epoxypropoxy)-coumarin (Example 29, Stage A) and dibutylamine. After recrystallisation from diisopropyl ether, a white product is obtained. Yield 30%. M.P. 78°–74° C.

Oxalate

Prepared according to the method of Example 3. M.P. 103°–105° C. (isopropanol).

EXAMPLE 69

3-(4'-Fluorophenyl)-4-(3''-morpholino-2''-methylpropoxy)-5,6,7,8-tetrahydrocoumarin

STAGE A.

3-(4'-Fluorophenyl)-4-hydroxy-5,6,7,8-tetrahydrocoumarin

Prepared by thermal condensation of ethyl p-fluorophenyl malonate and cyclohexanone in diphenyl ether. Yield 60%. M.P. 272° C.

STAGE B.

3-(4'-Fluorophenyl)-4-(3''-morpholino-2''-methylpropoxy)-5,6,7,8-tetrahydrocoumarin Prepared according to the method of Example 9 from 3-(4'-fluorophenyl)-4-hydroxy-5,6,7,8-tetrahydrocoumarin and 3-morpholino-2-methyl-1-chloropropane. A brown paste is obtained which cannot be crystallised. Yield 64%.

Oxalate

Prepared according to the method of Example 3. M.P. 192°–194° C. (methanol).

EXAMPLE 70

Bis-4,7-(3'-morpholino-2-methylpropoxy)-3-phenyl-coumarin

Prepared according to the method of Example 28 from 4,7-dihydroxy-3-phenyl-coumarin and 3-morpholino-2-methyl-1-chloropropane. Yield 85.4%. M.P. 128°–129° C. (isopropanol).

Dioxalate

Prepared according to the method of Example 3. M.P. 164°–167° C. (methanol).

What is claimed is:

1. A substituted pyranone represented by the formula:

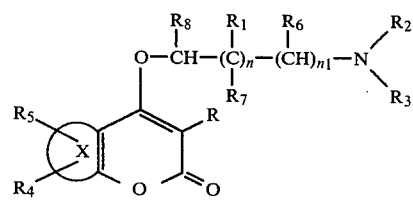

or a pharmaceutically acceptable acid addition salt thereof, wherein:

$n$ is 0 or 1;

$n_1$ is 0 or 1;

R is lower alkyl, phenyl, phenyl substituted by at least one halogen atom or lower alkoxy group, or benzyl;

$R_1$ is hydrogen, a hydroxy or lower alkyl group, or a 3,4,5-trialkoxybenzoyloxy radical;

$R_2$ is a straight-chain or branched lower alkyl group;

$R_3$ is hydrogen or lower alkyl; or $R_1$ and $R_2$ are joined together to form with the adjacent nitrogen atom a saturated heterocyclic ring with n being 1 and $n_1$ being 0, or $R_2$ and $R_3$ are joined together to form with the adjacent nitrogen atom a saturated heterocyclic ring optionally containing a further hetero atom;

X is benzene, cyclohexene, cycloheptene, cyclooctaene, cyclododecaene, naphthalene, dihydronaphthalene, or indeno (2,1-6) pyrano;

$R_4$ is H, halogen, hydroxy, lower alkyl, lower alkoxy, morpholinoalkoxy or phenyl;

$R_5$ is H, a substituent selected from hydroxy, straight-chain or branched lower alkyl, lower alkoxy and morpholinoalkoxy groups;

$R_6$ is hydrogen or a lower alkyl group;

$R_7$ is hydrogen or a lower alkyl group; and $R_8$ is hydrogen or a lower alkyl group.

2. A substituted pyranone represented by the formula:

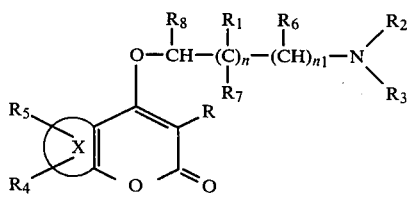

or a pharmaceutically acceptable acid addition salt thereof, wherein:

$n$ is 0 or 1;

$n_1$ is 0 or 1;

R is lower alkyl, phenyl, phenyl substituted by at least one halogen atom or lower alkoxy group, or benzyl;

$R_1$ is H, OH, lower alkyl or 3,4,5-trialkoxybenzoyloxy;

$R_2$ and $R_3$ together form morpholino;

X represents a benzene, cyclohexene, cycloheptene, cyclooctaene, cyclododecaene, naphthalene, dihydronaphthalene, 2-phenylindene or diphenyl ring;

$R_4$ is H, halogen, OH, lower alkyl, lower alkoxy or phenyl;

$R_5$ is H, OH, lower alkyl or lower alkoxy;

$R_6$ is hydrogen or a lower alkyl group;

$R_7$ is hydrogen or a lower alkyl group; and $R_8$ is hydrogen or a lower alkyl group.

3. A substituted pyranone represented by the formula:

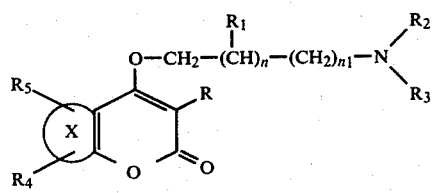

or a pharmaceutically acceptable acid addition salt thereof, wherein:

n is 0 or 1;

$n_1$ is 0 or 1;

R is phenyl;

$R_1$ is hydrogen, a hydroxy or lower alkyl group, or a 3,4,5-trialkoxybenzoyloxy radical;

$R_2$ and $R_3$ are joined together to form with the adjacent nitrogen atom a morpholino ring;

X represents a benzene, cyclohexene, cycloheptene, cyclooctaene, cyclododecaene, naphthalene, dihydronaphthalene, 2-phenylindene or diphenyl ring;

$R_4$ is H, OH, lower alkyl or lower akoxy; and $R_5$ is H, OH, lower alkyl or lower alkoxy.

4. A substituted pyranone represented by the formula:

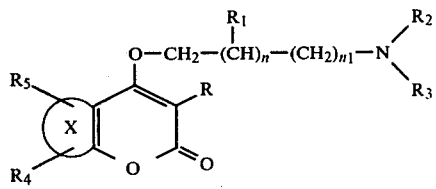

or a pharmaceutically acceptable acid addition salt thereof, wherein:

n is 0 or 1;

$n_1$ is 0 or 1;

R is phenyl;

$R_1$ is hydrogen, a hydroxy or lower alkyl group; or a 3,4,5-trialkoxybenzoyloxy radical;

$R_2$ and $R_3$ are joined together with the adjacent nitrogen to form morpholino or piperidino;

X is cyclohexene, cycloheptene, cyclooctaene or cyclododecaene;

$R_4$ is H, halogen, OH, lower alkyl, lower alkoxy or phenyl; and $R_5$ is H, OH, lower alkyl or lower alkoxy.

5. A compound in accordance with claim 4 of 4-(3'-piperidino-2'-hydroxy-propoxy)-3-phenyl-5,6,7,8-tetrahydro-coumarin, or a pharmaceutically acceptable acid addition salt thereof.

6. A compound in accordance with claim 4 of 3-phenyl-4-(2'-morpholino ethoxy)-[1-2-6]-cycloheptano-(2H)-pyran-2-one, or a pharmaceutically acceptable acid addition salt thereof.

* * * * *